United States Patent [19]
Alla et al.

[11] Patent Number: 5,596,087
[45] Date of Patent: Jan. 21, 1997

[54] PROCESS FOR THE PREPARATION OF BETA THYMIDINE

[75] Inventors: Venkata R. R. Alla; K. Gurjar Mukund; V. S. Lalitha Sista, all of Hyderabad, India

[73] Assignee: Council of Scientific & Industrial Research, New Delhi, India

[21] Appl. No.: 246,789

[22] Filed: May 20, 1994

[51] Int. Cl.$^6$ .......................... C07H 19/00; C07H 21/00
[52] U.S. Cl. .................. 536/22.1; 536/17.3; 544/310
[58] Field of Search .................. 544/310; 536/17.3, 536/22.1

[56] References Cited

U.S. PATENT DOCUMENTS

| | | | |
|---|---|---|---|
| 4,730,001 | 3/1988 | Shealy | 514/274 |
| 4,914,233 | 4/1990 | Freskos et al. | 536/23 |
| 4,916,218 | 4/1990 | Almond et al. | 536/18.2 |
| 4,921,950 | 5/1990 | Wilson | 536/23 |

OTHER PUBLICATIONS

Tatsuoka et al. Chem. Abst. 106: 156825 (1986).
Hrebabecky et al. Chem. Abst. 120: 54874 (1993).
Hrebabecky et al. Chem. Abst. 120: 8932 (1992).
Chu et al. Chem. Abst. 118: 169530 (1992).
Minamoto et al, Chem. Abst. 117: 70227 (1992).
Huss et al. Chem. Abst. 114: 207678 (1991).
Meguro et al. Chem. Abst 112: 217470 (1989).
Perlman et al. Chem. Abst. 111: 23863 (1989).
Lofthouse et al, Chem. Abst. 87: 85190 (1977).

*Primary Examiner*—Cecilia Tsang
*Attorney, Agent, or Firm*—Ladas & Parry

[57] ABSTRACT

Process for the preparation of beta-thymidine of the formula

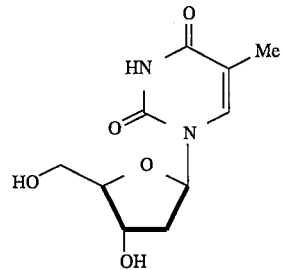

wherein Me represents methyl.

22 Claims, 2 Drawing Sheets

PROCESS FOR THE PREPARATION OF BETA THYMIDINE

FIELD OF THE INVENTION

The invention relates to an improved process for the preparation of beta-thymidine. Beta-thymidine prepared by the process of the present invention has the formula 2 shown in FIG. 1 of the drawing accompanying this specification wherein Me represents a methyl group. Beta-thymidine is an important intermediate for the preparation of dideoxy-nucleosides. Dideoxy-nucleosides of the formula 1 wherein X represents hydrogen or $N_3$, the base represents thymine, cytosine or hypoxanthine are of current interest because of their clinical use in the treatment of acquired immuno deficiency syndrome (AIDS).

DESCRIPTION OF THE PRIOR ART

AZT of the formula 1 wherein X represents $N_3$ and the base represents thymine, is the most active anti-AIDS agent. Many synthetic routes for preparing this compound have been reported (R. Benhaddou et al, Bull, Soc. Chim. Fr., 1991 (January-February), 108–11; J. D. Wilson, U.S. Pat. No. 4,921,950; Wellcome Foundation Ltd. Jp. Pat. No. 63,255,295; C. K. Chu, PCT Int. Appl. No. 9001,492; M. R. Almond et al, U.S. Pat. No. 4,916,218).

The commercially useful route for the preparation of AZT uses beta-thymidine of the formula 2 wherein Me represents methyl group as the starting material. (O. Szabolcs et al, Hung. Teljes, HU 48,901; S. Czernecki et al, Eur. Pat. No. 427,587; J. L. Rideout et al, Eur. Pat. No. 199,451; F. Y. Shealy et al, U.S. Pat. No. 4,730,001; J. N. Freskos et al, U.S. Pat. No. 4,914,233).

In U.S. Patent No. 4,914,233 a process has been disclosed for the synthesis of beta-thymidine in which a mixture of alpha and beta anomers of tetraacetylribofuranose of the formula 4 wherein R represents acetyl group is converted selectively to the desired beta-thymidine. The process involves the following steps (a) converting a mixture of alpha and beta anomers of tetra-O-acetylribofuranose to tri-O-acetyl-beta-ribothymidine, (b) converting tri-O-acetyl-beta-ribothymidine to beta-ribothymidine, (c) converting the beta-ribothymidine to 2,2'-anhydro-beta-thymidine, (d) converting 2,2'-anhydro-beta-thymidine to 2'-halo-2'deoxy-5-methylmidine and (e) converting 2'-halo-2'-deoxy-5-methylmidine to beta-thymidine.

The mixture of alpha and beta anomers can be prepared by any suitable methods such as by converting lower alkyl ribofuranoside to the tetra-O-acetyl ribofuranose mixture. The lower alkyl ribofuranosides may in turn be prepared by various known methods. The desired method may make use of D-ribose as the starting material which is then converted to the lower alkyl ribofuranoside.

The common way of preparing AZT from thymidine involves the preparation of 2,3'-anhydro derivative followed by the displacement reaction with sodium azide to furnish AZT.

SUMMARY OF THE INVENTION

Figure 1:
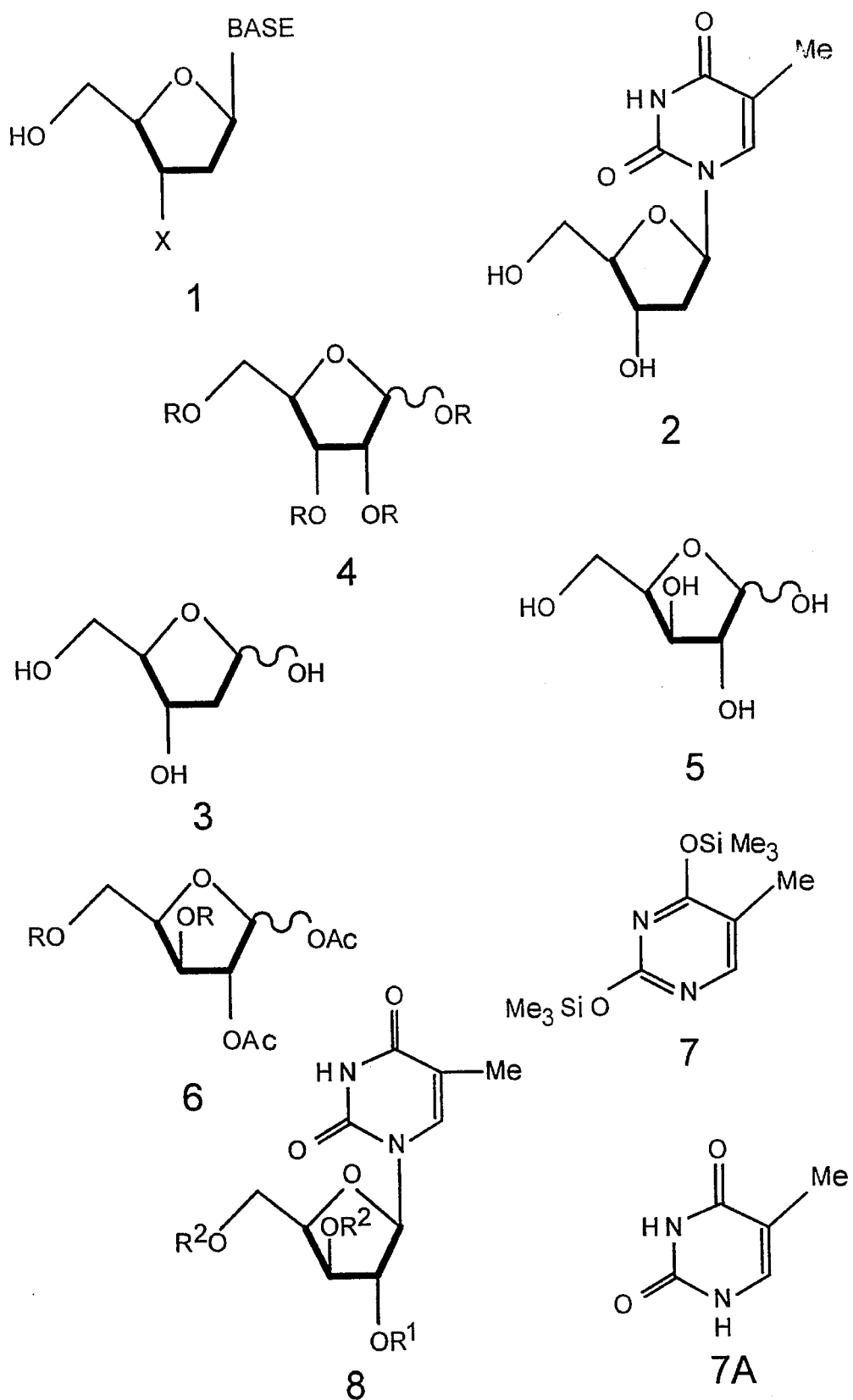
FIG. 1 show the formulas 1–8 referred to herein.
Figure 2:
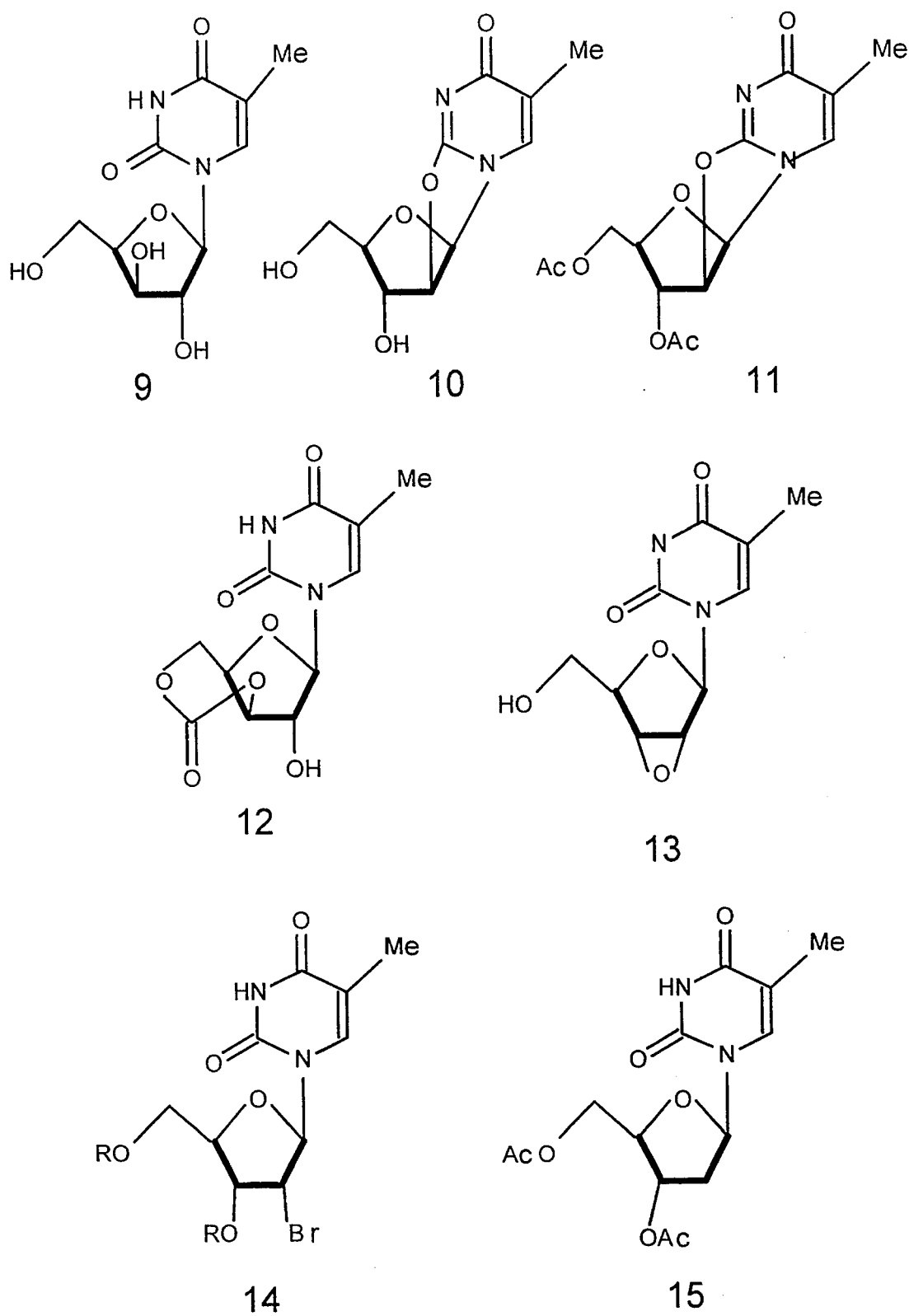
FIG. 2 shows the formulas 9–15 referred to herein.

Accordingly the present invention provides an improved process for the preparation of beta-thymidine of the formula 2 shown in FIG. 1 accompanying this specification wherein Me represents a methyl group, which comprises:

(a) preparing the deprotected xylothymidine of the formula 9 by removing, by conventional methods, the acyl group from 2,3,4-tri-O-acylxylothymidine of the formula 8 wherein $R^1$ represents acetyl group, $R^2$ represents benzoyl or acetyl group and Me represents methyl group, (b) condensing the deprotected xylothymidine of the formula 9 with condensing agents like dialkyl or diaryl carbonates in the presence of a base and an organic solvent to yield 2,2'-anhydrothymidine of the formula 10 wherein Me represents a methyl group, (c) brominating the 2,2'-anhydrothymidine of the formula X as defined above by conventional methods to afford a 2'-bromo derivative of the formula 14 wherein Br represents bromine, R represents an acetyl group of hydrogen and Me represents methyl group, (d) reducing the 2'-bromo derivative of the formula 14 by conventional methods to yield beta-thymidine of the formula 2 or its diacetyl derivative and (e) if desired, deacylating the acetyl derivative of the formula 15 wherein Ac represents an acetyl group by conventional methods to yield beta-thymidine of the formula 2 wherein Me represents a methyl group.

The 1,2,3-tri-O-acylxylothymidine of the formula 8 can be prepared by condensing a mixture of alpha and beta-1, 2,3,4-tetra-O-acylxylofuranose of the formula 6 wherein R represents a benzoyl group and Ac represents an acetyl group or by condensing a mixture of alpha and beta-1,2,3, 4-tetra-O-acetylxylofuranose of the formula 6 wherein R and Ac represent acetyl group with O,O-bis (trimethylsilyl) thymine of the formula 7 in the presence of condensing agents like Lewis acids.

The removal of acyl group from the compound of the formula 6 can be effected in the presence of a base such as sodium methoxide, ammonia, potassium carbonate and the like. The organic solvent employed may be selected from methanol, ethanol and the like. The condensing agent employed for condensing the compound of formula 9 may be selected from dialkyl or diaryl carbonate such as dimethyl, diethyl, diphenyl carbonate and the like.

The condensation of the formula 9 may be effected in the presence of base like sodium bicarbonate, sodium carbonate, potassium carbonate, and the like in the presence of polar aprotic solvents agents like N,N-di-methylformamide. The condensation may be effected at a temperature in the range of 120° to 160° C.

The bromination of formula 10 may be effected by employing agents like hydrogen bromide dissolved in an appropriate solvent, for example, N,N-dimethylformamide. The bromination may also be effected in the presence of agents such as pyridinium hydrobromide.

The bromo derivative may be reduced employing usually employed agents such as Raney Nickel, palladium on charcoal and the like. The deacetylation of the compound of the formula 15 may be effected using a base such as, for example, sodium methoxide or ammonia. Solvents such as, for example, methanol or ethanol may also be employed for the deacetylation.

DETAILED DESCRIPTION

The known syntheses of beta-thymidine of the formula 2 wherein Me represents methyl group are fraught with many difficulties, the foremost being expensive starting materials. For example beta-thymidine is prepared by the coupling reaction between protected 2-deoxy-D-ribose of the formula 3 and protected thymine of the formula 7 which unfortunately provided a mixture of alpha and beta nucleosides (A. J. Hubbard et al, Nucleic Acids Res. 1984, 12,682/; U. Nieball et al, J. Org. Chem. 1974, 39,3654; H. Vorbruggen et al, U.S. Pat. No. 3,748,320).

The alpha-nucleoside has very little use in the synthesis of pharmaceutically useful compounds. Moreover the separation of alpha and beta nucleosides is a tedious process.

The recently reported process for the preparation of beta-methymidine comprises the coupling reaction between protected D-ribose of the formula 4 wherein R represents acetyl group and protected thymine of the formula 7 followed by deoxygenation at C-2'. This process, though it does not produce alpha nucleoside, is still an expensive process as it uses D-ribose as a starting material.

D-xylose of the formula 5 may be converted into a mixture of alpha and beta 1,2-di-O-acetyl-3-5-di-O-benzoylxylofuranose of the formula 6 wherein R represents benzoyl group and Ac represents an acetyl group following the procedure described in J. Heterocyl, Chem. 1982, 19 (3), 597,602. The condensation of compound of formula VI with thymine of the formula 7A, may be effected in the presence of tin tetrachloride ($SnCl_4$), hexamethyldisilazane (HMDS) and trimethylsilylchloride (TMSCl). Reference in this connection may be made to J. Med. Chem. 1986, 29 (2), 203–209. The coupling can also be done by condensing the above xylose derivative of the formula 6 wherein R represents benzoyl and Ac represents an acetyl group with O,O-bis(trimethylsilyl) thymine of the formula 7 in the presence of $SnCl_4$. The removal of the acetyl or benzoyl groups from the resulting compound of formula 8 wherein $R^1$ represents an acetyl group and $R^2$ represents benzoyl group may be effected using a base such as sodium alkoxide or ammonia in methanol or potassium carbonate in methanol to provide xylothymidine of the formula 9 wherein Me represents a methyl group.

Alternatively 1,2,3,5-tetra-O-acetylxylofuranose of the formula 6 wherein R and Ac represent an acetyl group is condensed with protected thymine of the formula 7 and deacetylated under the conditions given above to provide xylothymidine of the formula 9 wherein Me represents a methyl group. The dialkyl or diaryl carbonates used for the condensation of xylothymidine may be dimethyl, diethyl or diphenylcarbonate. The condensation may be effected in the presence of sodium bicarbonate in N,N-dimethylformamide (DMF) at a temperature in the range of 120°–160° C. to give 2,2'-anhydrothymidine of the formula 10 wherein Me represents a methyl group which is acetylated with pyridine and acetyl anhydride to give 3',5'-di-O-acetyl-2,2'-anhydrothymidine of the formula X wherein Me represents a methyl group and Ac represents an acetyl group.

It is interesting to note that in the above reaction, wherein Me represents a methyl group a novel rearrangement via intermediates of the formula 12 and 13 occurs. The treatment of 2,2'-anhydrothymidine of the formula 10 or its diacetyl derivative of the formula 11 with hydrogen bromide in N,N-dimethylformamide may be effected at a temperature in the range of 90°–110° C. or with pyridinium-hydrobromide salt in pyridine at a temperature in the range of 110°–130° C. to afford the 2'-bromo derivative of the formula 14 wherein R represents an acetyl group. This compound is then reduced as such or as its diacetyl derivative in the presence of Raney Nickel or palladium on charcoal to afford beta-thymidine of the formula 2 or its diacetyl derivative of the formula 15 wherein Me represents a methyl group and Ac represents an acetyl group. Deacetylation of the compound of the formula 15 with mild base resulted in the formation of beta-thymidine of the formula 2.

The invention is described in detail in the examples given below which are provided to illustrate the invention only and therefore should not be construed to limit the scope of the present invention.

EXAMPLE I

Converting an anomeric mixture of tetra-O-acetylxylofuranose of the formula (6) to xylothymidine of the formula (9)

To a solution of 35 gm of tetra-O-acetylribofuranose in 130 ml in a round bottom flask equipped with a magnetic stir bar and nitrogen inlet, was added 36 gm (1.2 eqv) of O,O-bis(trimethylsilyl)thymine. To the slurry was added 14 ml (1.1 eqv) of tin tetrachloride in 25 ml of dichloromethane. The resulting clear solution was stirred at room temperature for 18 hrs, at the end of which thin layer chromatography (TLC) (2% MeOH in $CHCl_3$) showed no starting sugar. The reaction was quenched with 650 ml of saturated aqueous sodium bicarbonate solution. The mixture was filtered through celite to remove the tin salts. The organic layer, after separation was dried over sodium sulfate and concentrated to a light yellow foam (tri-O-acetylxylothymidine of the formula 8).

Crude tri-O-acetylxylothymidine (8) from the above reaction was dissolved in 300 ml of methanol and 0.525 gm (0.25 eqv) of sodium was added. After 8 hrs. TLC (10% MeOH in $CHCl_3$) showed no starting triacetate. The reaction was quenched with Amberlite IR 120 resin and filtered. The filtrate was concentrated to afford 21.5 gm of xylothymidine of the formula (9). (75% from tetra-O-acetylribofuranose).

EXAMPLE 2

Converting xylothymidine of the formula (9) to 2,2'-anhydrothymidine of the formula (10)

A mixture of 10 gm of xylothymidine, 9.9 gin (1.2 eqv) of diphenylcarbonate and 300 mg of sodium bicarbonate in 20 ml DMF was taken in a 250 ml round bottom flask equipped with a magnetic stirrer, reflux condenser and nitrogen inlet. The reaction mixture was heated to 150° C. for 4 hrs at the end of which TLC (1:9 MeOH in EtOAc) showed no starting triol. The black solution was diluted with 10 ml of methanol and slowly added to 500 ml of ice cold benzene with stirring. The precipitated product was filtered, washed with benzene, dried and chromatographed (Eluent: 8% MeOG in $CHCl_3$) to yield 4.9 gm (53%) of anhydrothymidine.

EXAMPLE 3

Converting 2,2'-anhydrothymidine of the formula (10) to 3'5'-di-O-acetyl-2,2'-anhydrothymidine of the formula (11)

To a solution of 4 gm of anhydrothymidine in 15 ml of pyridine was added 5.1 gm of acetic anhydride. The mixture was shifted at room temperature for 3 hrs. when TLC (1:9 MeOH in EtOAc) showed to anhydro thymidine. The reaction was quenched with 10 ml of methanol and the solvents removed under vacuo. The brown semi solid is refluxed thrice in 50 ml benzene to yield 5.1 gm (94%) of 3',5'-di-O-acetyl-2,2'-anhydrothymidine of the formula (11). m.p. 168°–172° C.

EXAMPLE 4

Converting xylothymidine of the formula (9) to 3',5'-di-O-acetyl-2,2'-anhydrothymidine of the formula (1)

A 250 ml round bottom flask equipped with a magnetic stir bar, reflux condenser and nitrogen inlet was charged with 10 gm of xylothymidine of the formula (9), 9.9 gm (1.2 eqv) of diphenyl carbonate and 300 mg sodium bicarbonate in 20 ml DMF and was heated to 150° C. for 4 hrs. when TLC (1:9 MeOH in EtOAc) showed no starting xylothymidine. The reaction mixture was cooled and added dropwise into 600 ml ice cold benzene with stirring. The solid was filtered and dissolved in 30 ml pyridine. To the above stirred solution was added 12 gm acetic anhydride. After 3 hrs. the reaction was quenched with 20 ml methanol, concentrated to dryness and the semisolid refluxed thrice in benzene (100 ml) to yield 4.8 gm of 3',5'-di-O-acetyl-2,2'-anhydrothymidine of the formula (11). m.p. 168°–171° C.

EXAMPLE 5

Converting 3',5'-di-O-acetyl 2,2'-anhydro thymidine of the formula (11) to 2'-bromo-2'-deoxy-3'5'-di-O-acetylthymidine of the formula (14).

Diacetylanhydrothymidine of the formula (11) (5 g) was dissolved in 20 ml of DMF containing 1.5 gm (1.2 eqv) of anhydrous HBr and kept at 90°–110° C. for 2 hrs. The reaction mixture was poured into 100 ml ice water, extracted thrice with chloroform (30 ml), the organic layers combined, dried and concentrated to yield 5.9 gm (95%) of 2'-bromo-2'-deoxy-3',5'-di-O-acetylthymidine of the formula (14).

EXAMPLE 6

Converting 2'-bromo-2'-deoxy-3'5'-di-O-acetylthymidine of the formula (14) to beta-thymidine of the formula (2):

5 gin of 2'-bromo-2'-deoxy-3',5'-di-O-acetylthymidine of the formula (14) was hydrogenated in a Parr apparatus at 40 psi in the presence of 5 gm Raney-Nickel in 30 ml methanol. After 4–5 hrs the reaction mixture was filtered through celite, concentrated, redissolved in 30 ml ethylacetate and washed thrice with water (30 ml). The organic layer was dried over sodium sulfate and concentrated to give 3',5'-di-O-acetylthymidine of the formula (15).

Crude 3',5'-di-O-acetylthymidine was dissolved in 20 ml methanol, and 0.075 gm sodium was added. After 8 hrs the reaction was quenched with Amberlite IR 120 resin, filtered and concentrated to yield beta-thymidine (2.4 gm, 80%). m.p. 181°–183° C.

We claim:
1. A process for the preparation of beta-thymidine of formula 2

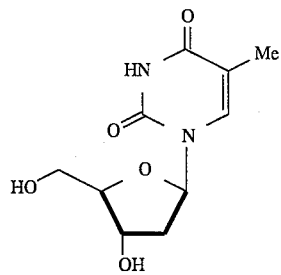

wherein, Me represents methyl, said process comprises:
(a) preparing deprotected xylothymidine of formula 9

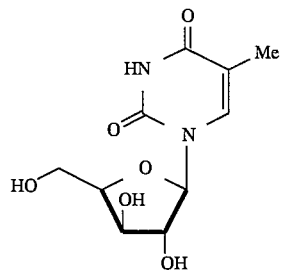

by removing by conventional methods, the acyl group from 1,2,3-tri-O-acyl-xylothymidine of formula 8

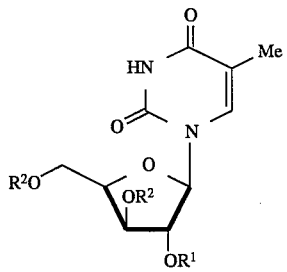

wherein $R^1$ represents acetyl, $R^2$ represents benzoyl or acetyl and Me represents methyl;
(b) condensing the deprotected xylothymidine of formula 9 with dialkyl or diaryl carbonate in the presence of a base and an organic solvent to yield 2,2'-anhydrothymidine of formula 10

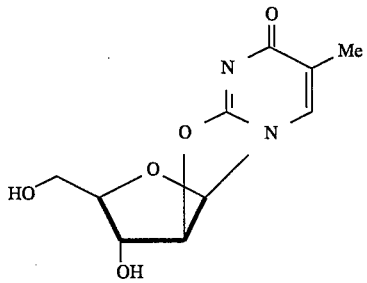

wherein Me represents methyl;

(c) brominating the 2,2'-anhydrothymidine of formula 10

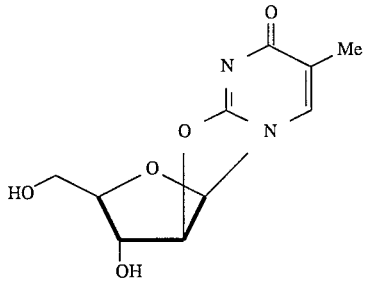

as defined above by conventional methods to form 2'-bromo compound of formula 14

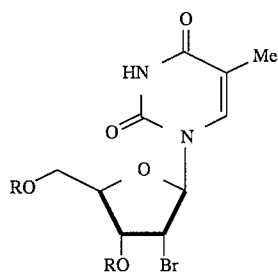

wherein R represents hydrogen or acetyl, Br represents bromine and Me represents methyl, (d) reducing the 2'-bromo compound of the formula 14 by conventional methods to yield beta-thymidine of formula 2

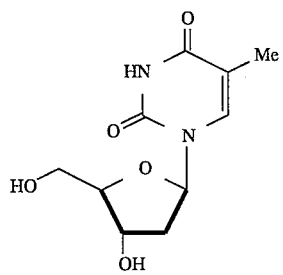

or its diacetyl compound, 15

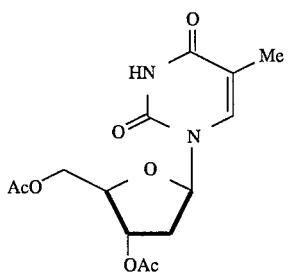

wherein Ac represents acetyl; and (e) if desired, deacylating the acetyl groups of the formula 15 by conventional methods to yield beta-thymidine of the formula 2

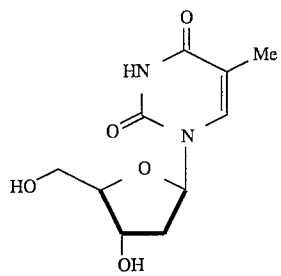

2. The process as claimed in claim 1 wherein the 1,2,3-tri-O-acyl-xylothymidine of the formula 8

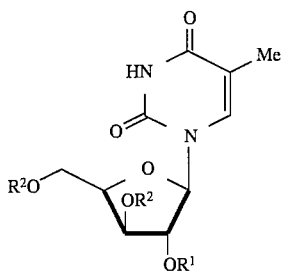

prepared by condensing a mixture of alpha and beta-1,2,-di-O-acetyl-3,5-di-O-benzoyl xylofurnaose of formula 6

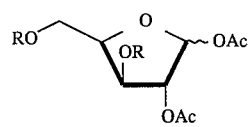

wherein R represents benzoyl and Ac represents acetyl or a mixture of alpha and beta-1,2,3,4-tetra-O-acetylxylofuranose of the formula VI wherein R and Ac each represent acetyl with O,O-bis(trimethylsilyl)thymine of the formula 7

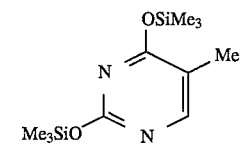

in the presence of a condensing agent.

3. The process as claimed in claim 2 wherein the condensing agent employed is selected from Lewis acids.

4. The process according to claim 3 where the Lewis acid is $SnCl_4$.

5. The process as claimed in claim 1 wherein the removal of acyl group from the compound of the formula VIII is effected in the presence of a base.

6. The process as claim in claim 5 wherein the base is selected from sodium methoxide, ammonia, or potassium carbonate.

7. The process as claimed in claim 1 wherein the organic solvent is selected from methanol or ethanol.

8. The process as claimed in claim 1 wherein the dialkyl or diaryl carbonate employed for condensing the formula 9 is selected from dimethyl, diethyl or diphenyl carbonate.

9. The process as claimed in claim 1 wherein the condensation of the compound of the formula 9 is effected in the presence of the base sodium bicarbonate.

10. The process as claimed in claim 1 wherein the condensation is effected in the presence of polar aprotic solvents.

11. The process as claimed in claim 10 wherein the polar aprotic solvent is N,N-dimethyl formamide.

12. The process as claimed in claim 1 wherein the condensation is effected at a temperature in the range of 120° to 160° C.

13. The process as claimed in claim 1 wherein the bromination is effected by employing a brominating agent.

14. The process as claimed in claim 13 wherein the brominating agent is selected from hydrogen bromide or pyridinium hydrobromide.

15. The process as claimed in claim 1 wherein a solvent is used in the bromination step.

16. The process as claimed in claim 15 wherein the solvent is N,N-dimethylformamide, pyridine or a mixture thereof.

17. The process as claimed in claim 1 wherein the bromo derivative is reduced by employing a reducing agent.

18. The process as claimed in claim 17 wherein the reducing agent is Raney Nickel or palladium on charcoal.

19. The process as claimed in claim 1 wherein the deacetylation Of the compound of the formula 15 is effected using a base.

20. The process as claimed in claim 19 wherein the base is sodium methoxide or ammonia.

21. The process as claimed in claim 1 wherein the solvents employed for the deacetylation are methanol or ethanol.

22. In a process for the preparation of beta-thymidine of formula 2

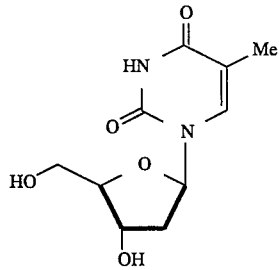

wherein Me represents methyl; preparing deprotected xylothymidine of formula 9

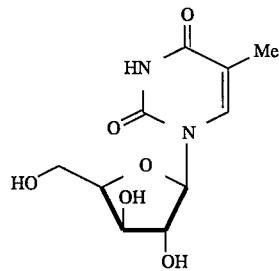

removing the acyl group from 1,2,3-tri-O-acylxylothymidine of formula 8

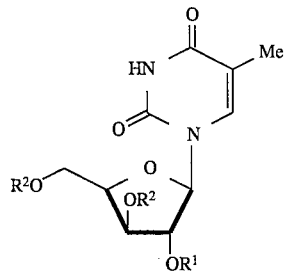

wherein $R^1$ represents acetyl, $R^2$ represents benzoyl or acetyl and Me represents methyl, preparing compound of formula 10

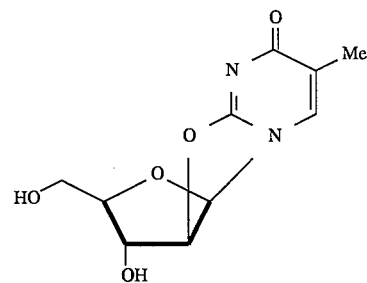

from formula 9 brominating the 2'2 anhydrothymidine of formula 10 to form 2'-bromo compound of formula 14

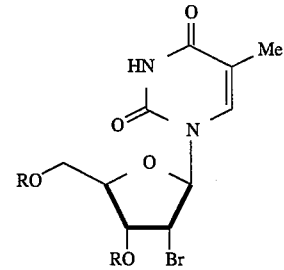

wherein R represents hydrogen or acetyl, Br represents bromine and Me represents methyl, reducing the 2'-bromo compound of the formula 14 to yield beta-thymidine of formula 2

11

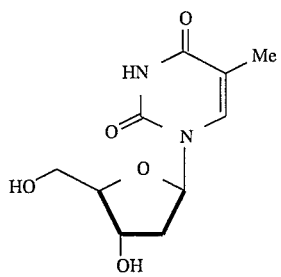

or its diacetyl compound 15

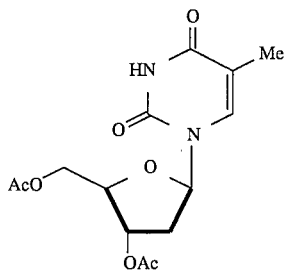

12

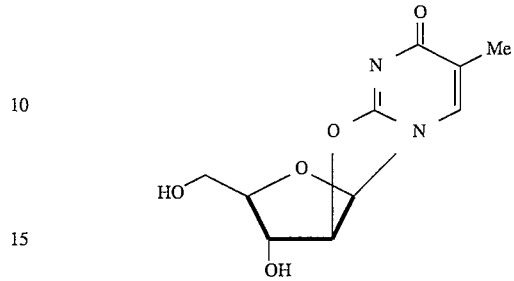

wherein Ac represents acetyl; if desired deacylating the acetyl groups of the formula 15 to yield beta-thymidine of formula 2 wherein the improvement comprises preparing 2,2'-anhydrothymidine of formula 10 by condensing the deprotected xylothymidine of formula 9 with dialkyl or diaryl carbonate in the presence of a base and an organic solvent to yield 2,2'anhydrothymidine of formula 10.

* * * * *